(12) United States Patent
Syroid et al.

(10) Patent No.: US 9,277,890 B2
(45) Date of Patent: Mar. 8, 2016

(54) SYSTEM FOR GENERATING NONINVASIVE RESPIRATORY MONITOR SIGNALS

(71) Applicant: Dynasthetics, LLC, Salt Lake City, UT (US)

(72) Inventors: Noah Syroid, Cottonwood Heights, UT (US); Joseph Orr, Park City, UT (US)

(73) Assignee: Dynasthetics, LLC, Salt Lake City, UT (US)

( * ) Notice: Subject to any disclaimer, the term of this patent is extended or adjusted under 35 U.S.C. 154(b) by 129 days.

(21) Appl. No.: 13/874,030

(22) Filed: Apr. 30, 2013

(65) Prior Publication Data

US 2014/0243629 A1 Aug. 28, 2014

Related U.S. Application Data

(60) Provisional application No. 61/768,654, filed on Feb. 25, 2013.

(51) Int. Cl.

| *A61B 5/00* | (2006.01) |
|---|---|
| *A61B 5/1455* | (2006.01) |
| *A61M 16/00* | (2006.01) |
| *A61M 16/20* | (2006.01) |
| A61M 16/12 | (2006.01) |
| A61B 5/087 | (2006.01) |
| G09B 23/30 | (2006.01) |

(52) U.S. Cl.
CPC ........... *A61B 5/7278* (2013.01); *A61B 5/14552* (2013.01); *A61B 5/4836* (2013.01); *A61M 16/0051* (2013.01); *A61M 16/12* (2013.01); *A61M 16/204* (2014.02); *A61B 5/087* (2013.01); *A61B 5/6826* (2013.01); *A61M 16/122* (2014.02); *A61M 2016/0027* (2013.01); *A61M 2016/0039* (2013.01); *A61M 2202/0225* (2013.01); *A61M 2205/502* (2013.01); *A61M 2230/205* (2013.01); *A61M 2230/432* (2013.01); *G09B 23/303* (2013.01)

(58) Field of Classification Search
CPC ...... G09B 23/00; G09B 23/303; A61B 5/145; A61B 5/14542; A61B 5/14551
USPC .......................................................... 434/268
See application file for complete search history.

(56) References Cited

U.S. PATENT DOCUMENTS

| 5,403,192 | A | * | 4/1995 | Kleinwaks et al. | 434/272 |
|---|---|---|---|---|---|
| 5,941,710 | A | * | 8/1999 | Lampotang et al. | 434/272 |
| 5,975,748 | A | * | 11/1999 | East et al. | 703/6 |
| 7,959,443 | B1 | * | 6/2011 | Frembgen et al. | 434/265 |
| 8,500,452 | B2 | * | 8/2013 | Trotta et al. | 434/268 |
| 2006/0247507 | A1 | * | 11/2006 | Ruiter | 600/331 |
| 2010/0324387 | A1 | * | 12/2010 | Moon et al. | 600/324 |
| 2011/0213227 | A1 | * | 9/2011 | Ziv et al. | 600/323 |
| 2012/0184832 | A1 | * | 7/2012 | Diab et al. | 600/331 |
| 2012/0197580 | A1 | * | 8/2012 | Vij et al. | 702/114 |

* cited by examiner

*Primary Examiner* — Peter Egloff
(74) *Attorney, Agent, or Firm* — Snow, Christensen & Martineau; Christopher L. Wight

(57) ABSTRACT

A system for simulating various clinical conditions which are detectable by a noninvasive respiratory monitor is provided. The simulated clinical conditions may be displayed on a noninvasive respiratory monitor to replicate a variety of disease states to provide training for a clinician. The system may include a pulse oximetry simulation device and/or a $CO_2$ delivery system.

4 Claims, 5 Drawing Sheets

SYSTEM FOR GENERATING NONINVASIVE RESPIRATORY MONITOR SIGNALS

THE FIELD OF THE INVENTION

The present invention relates to a system for generating noninvasive respiratory monitor signals.

BACKGROUND

Respiratory failure can become a life-threatening condition in a few minutes or be the result of a build up over several hours. Respiratory failure is very difficult to predict, and as a result continuous monitoring of respiratory activity is typically necessary in clinical, high-risk situations. Appropriate monitoring equipment used by properly trained clinicians can be life-saving. (see Folke M, Cernerud A, Ekstrom M, Hok B; Critical Review of Non-invasive Respiratory Monitoring in Medical Care; Medical & Biological Engineering & Computing 2003 July; 41(4): 377-383).

Noninvasive patient respiratory monitors are especially useful in situations when drugs having sedative and/or analgesic properties are provided to a patient because these drugs may also reduce the patient's drive to breath and ability to maintain an open airway. Noninvasive respiratory monitors may be used to measure the patient's respiratory rate and exhaled $CO_2$ by analyzing the concentration of the $CO_2$ in the exhaled air. They may also be used to monitor heart rate and saturation of blood oxygen. In other words, noninvasive respiratory monitors are configured to provide multiple indications regarding the physical state of a patient It is important that a clinician be able to properly analyze all the information provided by a noninvasive respiratory monitor. The American Society of Anesthesiologists emphasizes that, because ventilation and oxygenation are separate physiologic processes, monitoring oxygenation by pulse oximetry is not a substitute for monitoring ventilatory function by capnography. (see Practice guidelines for sedation and analgesia by non-anesthesiologists. American Society of Anesthesiologists Task Force on Sedation and Analgesia by Non-Anesthesiologists. Anesthesiology 2002; 96: 1004-1017). Oxygen saturation usually is maintained, even at a low respiratory rate, so that pulse oximetry might fail to detect respiratory deterioration, particularly if a patient is receiving supplemental oxygen. (see Overdyk F J. PCA presents serious risks. [letter] APSF Newsletter 2005; 20: 33). The use of supplemental oxygen does not correct desaturation due to hypoventilation; it simply delays the progression of respiratory failure from bradypnea to apnea. Thus, even continuous monitoring of heart rate and oxygen saturation ("$SpO_2$") by pulse oximetry is not a substitute for monitoring end-tidal $CO_2$ ("$EtCO_2$"), respiratory rate, and apneic events by capnography. Capnographic monitoring can anticipate a patient's desaturation by warning of a decrease in respiratory rate and rise in $EtCO_2$. (see Weinger M B. Dangers of postoperative opioids. Anesthesia Patient Safety Foundation newsletter 2006-2007; 21: 61-88). In a procedural sedation study, pulse oximetry identified only 33 percent of those patients with respiratory distress, while capnography captured 100 percent. (see Miner J R, Heegaard W, Plummer D. End-tidal carbon dioxide monitoring during procedural sedation. Acad Emerg Med 2002; 9: 275-280). Therefore, it is important that a clinician be proficient at analyzing all the data that can be obtained from a noninvasive respiratory monitor.

Additionally, there are numerous manufactures of noninvasive respiratory monitors, for example, COSMO by Novametrix Medical Systems, Inc., Wallingford, Conn.; Capnostream by Oridion Capnography, Inc., Bedford, Mass.; POET by Criticare Systems, Inc., Waukesha, Wis., etc. Thus, as will be appreciated from the foregoing, one drawback of using noninvasive respiratory monitors is that significant training may be needed before a clinician can make full use of the information provided by these monitors.

Thus there is a need for a system for generating noninvasive respiratory monitor signals to simulate patient conditions encountered by clinicians in order to train the clinician in the proper use of a particular noninvasive respiratory monitor.

SUMMARY OF THE INVENTION

It is an object of the present invention to provide system for generating noninvasive respiratory monitor signals.

According to one aspect of the invention, a system is provided which may simulate various clinical conditions that may be used to display parameters and waveforms on a noninvasive respiratory monitor. The system may be configured to cause a noninvasive respiratory monitor to display realistic parameters and waveforms consistent with disease states to provide essential training for a clinician.

According to another aspect of the invention, the system may physically re-create signals so that they can be displayed on a variety of noninvasive respiratory monitors.

According to another aspect of the invention, the system may include a pulse oximetry simulation device that may be configured to correctly operate interchangeably with a variety of pulse oximeters even if they have different timing and/or sequencing schemes.

According to another aspect of the invention, the system may use potentiometer(s) to control the amount of transmitted light by a pulse oximetry simulation device.

According to another aspect of the invention, the system may include a $CO_2$ delivery system for delivering a flow of air having a desired $CO_2$ concentration to a noninvasive respiratory monitor.

According to another aspect of the invention, a $CO_2$ delivery system may use one or more flow sensors in combination with one or more valves to control the concentration of $CO_2$ in a flow of air.

According to still another aspect of the invention, the system may include two flow sensors to separately measure the flow of air and the flow of $CO_2$. The ratio of the measured flows may be calculated by a computer system and used to adjust the signal transmitted to a valve that controls the flow of $CO_2$ and/or air in order to deliver a desired $CO_2$ concentration to a noninvasive respiratory monitor.

According to yet another aspect of the invention, a system may include a pulse oximetry simulation device and a $CO_2$ delivery system to create signals that are detected by a noninvasive respiratory monitor. The noninvasive respiratory monitor may use the detected signals to calculate clinical parameter such as $SpO_2$, heart rate, $EtCO_2$ and respiratory rate to generate a capnogram for $CO_2$ and arterial plethysmogram for oximetry.

These and other aspects of the present invention are realized in a system for generating noninvasive respiratory monitor signals to simulate patient conditions encountered by clinicians in order to train the clinician in the proper use of a particular noninvasive respiratory monitor as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
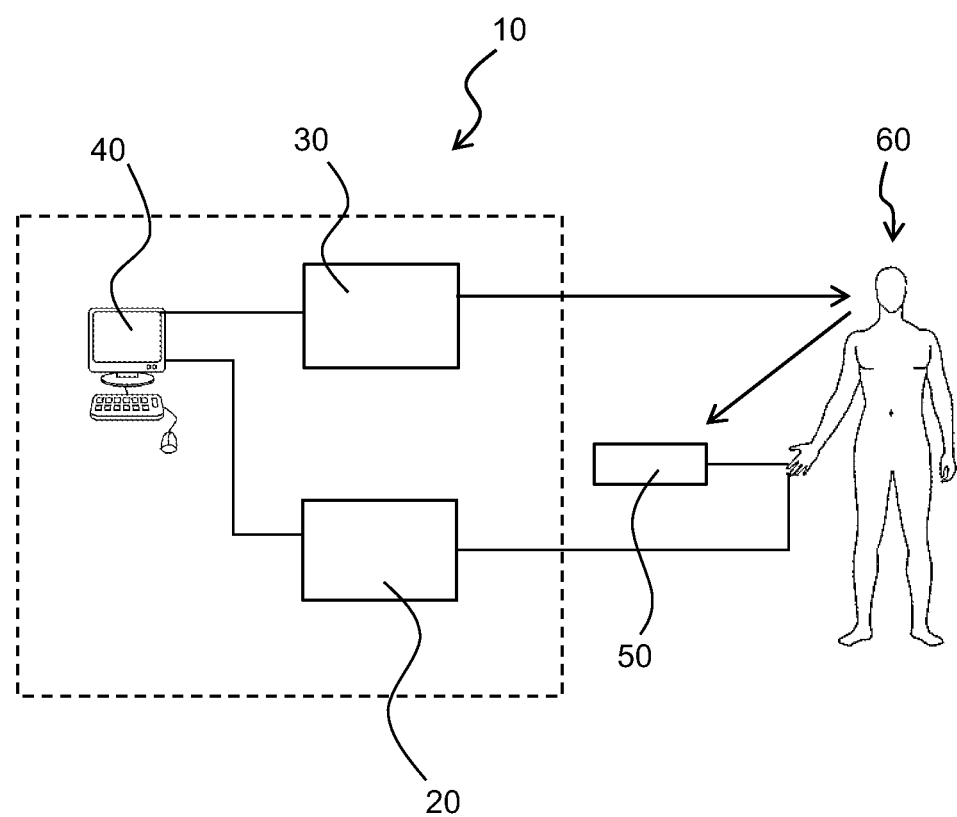
FIG. 1 shows a diagram of a system for generating noninvasive respiratory monitor signals according to principles of the present invention.

Turning now to FIG. 1, a diagram is shown of a system for generating noninvasive respiratory monitor signals, generally indicated at 10, according to principles of the present invention. The system 10 may be able to physically produce signals that are detectable by a noninvasive respiratory monitor 50. According to one aspect of the invention, the system 10 may include a computer 40 which may be used in connection with a device 20 to generate a signal that may be detected by a pulse oximeter of a noninvasive respiratory monitor 50. The device 20 may be able to function interchangeably with a variety of pulse oximeters 50 without reconfiguration of the device 20. For example, (and as will be explained in more detail below) the device 20 may be able to cause different pulse oximeters 50 to produce desired outputs by generating a signal that correlates with the timing and/or sequencing scheme of different pulse oximeters 50. In other words, the device 20 may have built-in adaptability for the different timing and/or sequencing schemes of commercially available pulse oximeters 50.

Additionally, system 10 may include a $CO_2$ delivery system 30 which may function in association with the computer 40 to deliver a flow of air having a desired $CO_2$ concentration to the noninvasive respiratory monitor 50. A $CO_2$ monitor, i.e. a capnometer, disposed on the noninvasive respiratory monitor 50 is able to detect the amount of $CO_2$ present in the flow of air. Data regarding the $CO_2$ concentration may then be provided to, for example, a clinician being trained to use a noninvasive respiratory monitor.

The system 10 may be able to alter the parameters of the signals produced and thereby simulate a variety of disease states that patient(s) 60 may present with in clinical situations. Thus, the system 10 may be used to train clinicians how to properly analyze information provided by noninvasive respiratory monitors.

Figure 2:
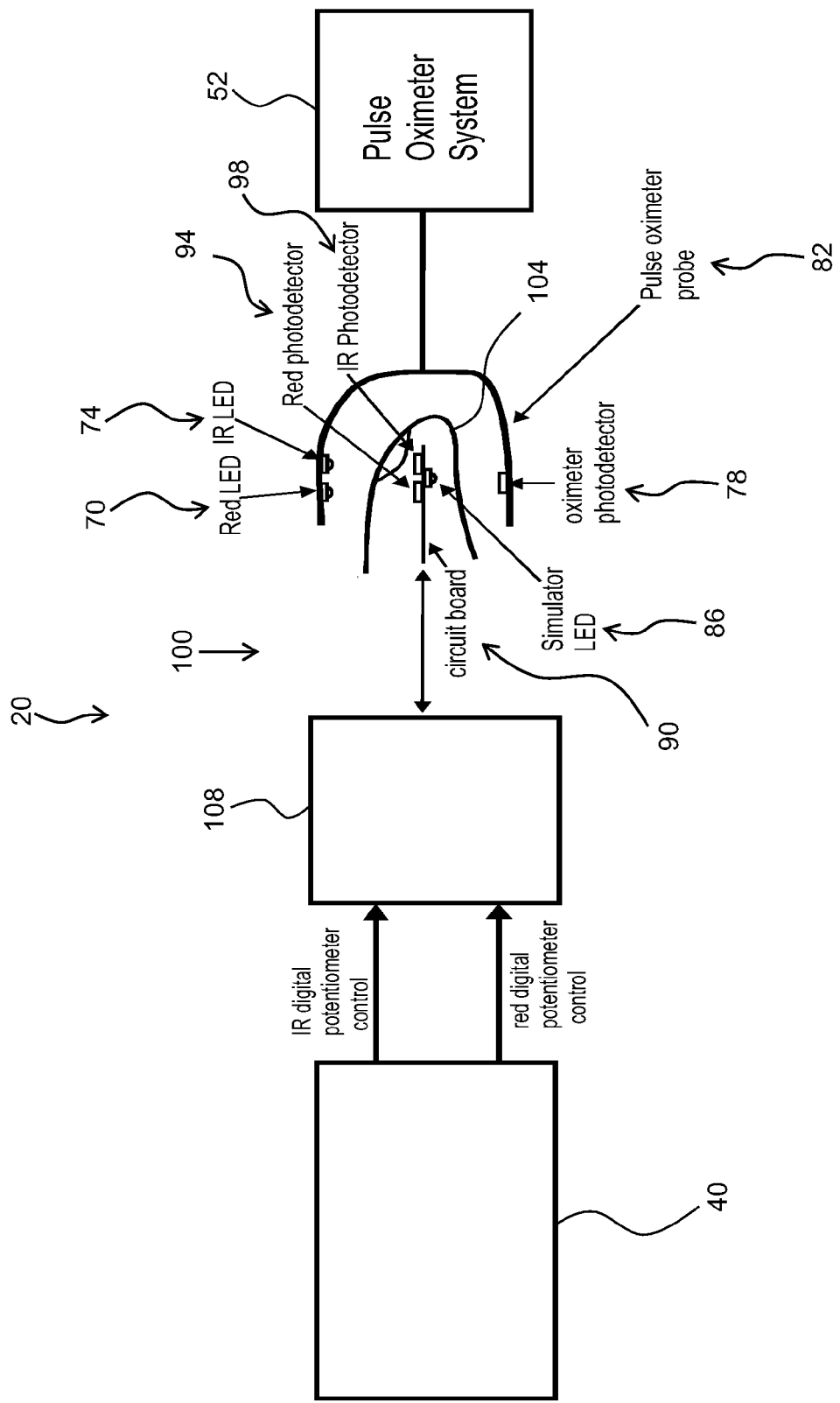
FIG. 2 shows a pulse oximetry simulation system according to principles of the present invention.

Turning now to FIG. 2, a pulse oximetry simulation device, generally indicated at 20, according to principles of the present invention is shown. A pulse oximeter 52 is a medical device that indirectly monitors the oxygen saturation of a patient's blood (as opposed to measuring oxygen saturation directly through a blood sample) and changes in blood volume in the skin, producing a plethysmogram. Typically a pulse oximeter includes a probe 82 comprising a pair of small light-emitting diodes (LEDs) 70, 74 facing a photodetector 78, such as a photodiode. The probe 82 is placed on a translucent part of the patient's body, usually a fingertip or an earlobe. However, one of skill in the art will appreciate that other monitoring sites are possible. One LED 70 is typically red, i.e. the LED 70 typically emits a light wavelength of about 630-660 nm. The other LED 74 is typically infrared (IR), i.e. the LED 74 typically emits a light wavelength of about 905-940 nm. Absorption at these wavelengths differs significantly between oxyhemoglobin and its deoxygenated form; therefore, the oxy/deoxyhemoglobin ratio can be calculated from the ratio of the absorption of the red and IR light.

The pulse oximeter 52 performs this measurement by sequentially turning on a red LED 70, and an IR LED 74 many times a second. The intensity of the light detected by the photodector 78 on the other side of the finger, ear lobe, etc., in response to turning on these LEDs may then be analyzed. The ratio of the pulsatile portion of the detected signals corresponding to the red LED 70 and IR LED 74 may be used to calculate blood oximetry. The shape of the detected pulse waveform for either the red or IR signal may also be used to calculate heart rate.

There are many manufacturers of pulse oximetry systems 52. Each of the various pulse oximeters may incorporate a specific timing and/or sequencing scheme for turning on the red LED 70 and IR LED 74. Thus, according to one aspect of the invention the pulse oximetry simulation system 20 may be configured to correctly operate interchangeably with a variety of pulse oximeters even if they have differing timing and/or sequencing schemes. Prior knowledge of the specific timing scheme of a particular pulse oximeter 52 may not be necessary. This is because a circuit (e.g. an analog circuit), generally indicated at 100, may be used to detect red or IR light emitted from a pulse oximeter and, in response, substantially simultaneously emits an appropriate intensity of red and/or IR light on the opposite side of the simulated finger where it is detected by the photodetector 78. Thus, the desired oxygen saturation and heart rate can be measured by the pulse oximeter 52 and displayed on its monitor.

Figure 3:
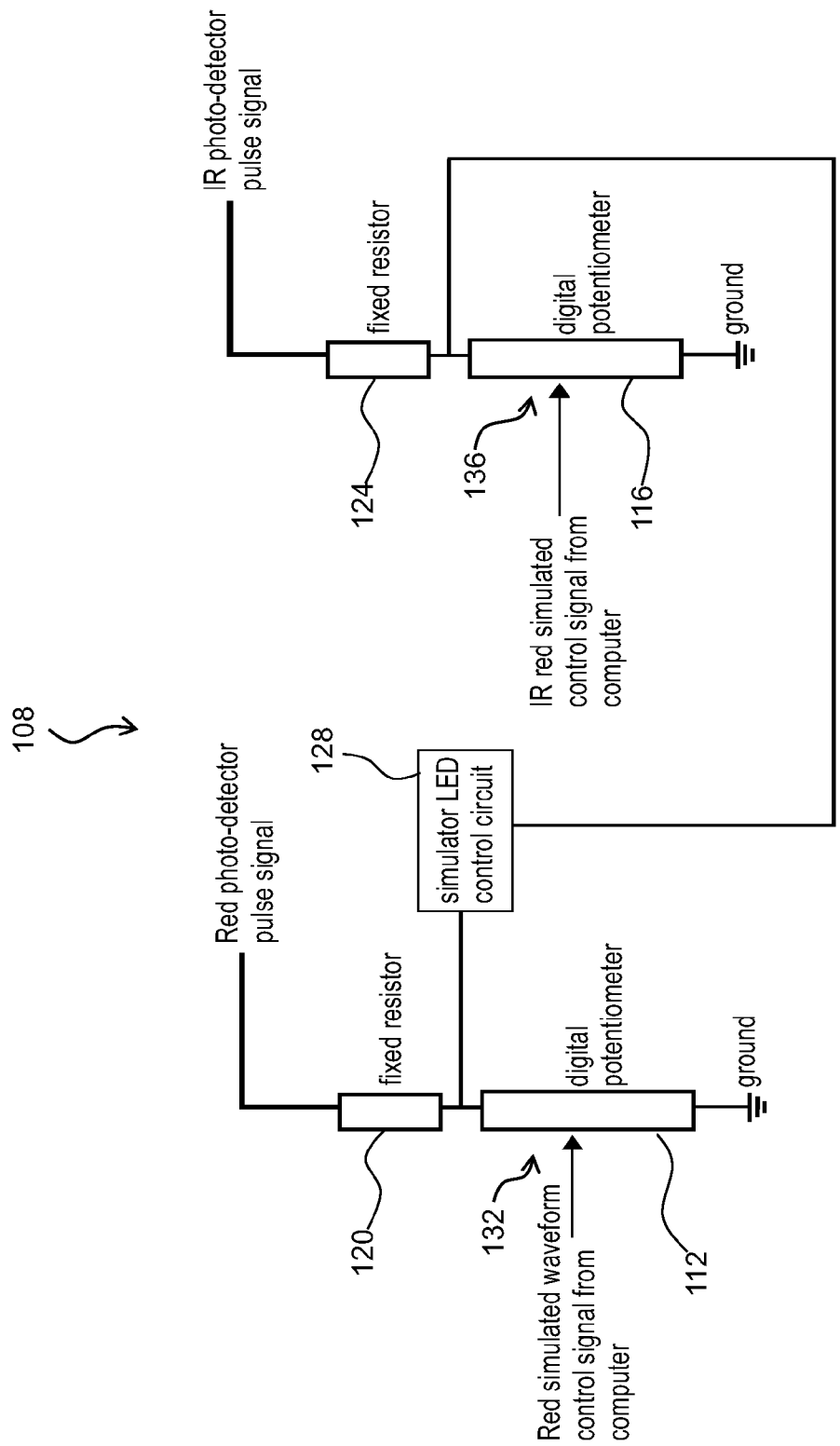
FIG. 3 shows an example of digital potentiometer circuit according to principles of the present invention.

The circuit 100 may comprise a simulation circuit 108. An exemplary simulation circuit 108 is shown in more detail in FIG. 3. The simulation circuit 108 may be in communication with a computer that contains the red and IR waveforms associated with a variety of disease states presented by patient(s). The computer may control the resistance of potentiometer(s) 112, 116 (e.g. digital potentiometer(s)) associated with the simulation circuit 108. For example, the computer may control a digital potentiometer 112 for the detected red light and a digital potentiometer 116 for the detected IR light. As shown in FIG. 3, the digital potentiometers 112, 116 may be connected in a circuit (e.g. an integrated circuit). The digital potentiometers 112, 116 may act as resistors where the amount of resistance in Ohms may be settable by the computer to control the intensity of light transmitted by the simulator LED 86 (FIG. 2).

Referring now to both FIG. 2 and FIG. 3, the simulation circuit 108 may be connected to a small printed circuit board 100 that is placed in, for example, a manikin finger 104 that allows red and IR light to pass though the simulated tissue. On one side of the printed circuit board 100 there may be located one or more photodetectors 94, 98 to detect red and IR light at the wavelengths used by the pulse oximeter 52. On the opposite side of the printed circuit board 100 there may be located a LED 86 for emitting red and IR light at an intensity that may be controlled by the simulation circuit 108.

The pulse oximeter may activate the red and/or IR LEDs 70, 74 multiple times each second in a sequence and duration that may be specific to each pulse oximeter manufacturer. The amount of light that is transmitted through the tissue in response to the specific LED (red 70 or IR 74) that has been activated is then detected by the photodetector 78 of the pulse oximeter 52.

The simulator device 20 detects the light from the LEDs 70, 74 that are controlled by the pulse oximeter 52. When red and/or IR light is detected, a voltage pulse corresponding to the detected light wavelength may be transmitted from the detector circuit through fixed resistor(s) 120, 124 and digital potentiometer(s) 112, 116. The voltage pulse created by the detected red or IR light may be at a fixed voltage (e.g. 5 volts) or they may be in proportion to the intensity of the detected light. In normal tissue the majority of the light from the LEDs 70, 74 of the pulse oximeter 52 may be dissipated in tissue and venous blood. Therefore, fixed resistor(s) 120, 124, which may dissipate red and/or IR signal from the photodetectors 94, 98, may be used to simulate this effect.

The resistance of the digital potentiometer(s) 112, 116 may be used to determine what fraction of the voltage pulse is then transmitted to the simulator LED control circuit 128 to control the intensity of light which is emitted from the simulator LED 86. Thus, the computer system 40 may not need to know the timing and/or sequence of the pulse oximeter 52 LED control.

As discussed briefly above, according to another aspect of the invention a pulse oximetry simulation system 20 may include a computer system 40 which may contain a stored waveform corresponding to what is observed when blood pulses through tissue (e.g. a pulsatile signal). The waveform may be generated from a known stored arterial pressure waveform. Alternatively, the computer 40 may be used to synthesize a waveform. It will be appreciated that there may be many ways to generate a pulsatile signal, and the discussion herein relating to pulsatile signal generation is not intended to limit the scope of the invention.

A variety of pulsatile signals may be stored in computer memory. For example, a first pulsatile signal may be stored in computer memory along with a second pulsatile signal which may be a separate, scaled version of the first pulsatile signal. In other words, the second pulsatile signal may have pulsations which are larger or smaller than the first pulsatile signal. The first signal may be transmitted to a digital potentiometer circuit 132 connected to the red light photodetector circuit, and the second signal, scaled up (larger amplitude) or down (smaller amplitude), may be transmitted to the digital potentiometer circuit 136 connected to the IR photodetector circuit. The ratio of the amplitude of the simulated pulsations of the first and second signals may then be used to determine the oxygen saturation (or SpO$_2$) calculated by the pulse oximeter 52. Additionally, the frequency of the pulsations may be used to determine the simulated heart rate.

It will be appreciated that the output of the digital potentiometer circuits 132, 136 may be connected to drive a single LED 86. Alternatively, separate LEDs could be used for each circuit provided that the separate LEDS are in close physical proximity. Additionally, it will be appreciated that a single circuit could drive multiple LEDs.

According to one aspect of the invention, the photodetectors of the pulse oximetry simulation system 20 may be configured to detect light wavelengths in a variety of fashions. For example, the red detector 94 may respond to both red and IR light, (i.e. the red detector 94 may detect multiple light wavelengths). The IR detector 98 may be configured with an optical filter such that it only responds to IR light. Additionally, a logic circuit, such as a simple digital logic circuit, may be used to convert the signals from the photodetectors such that the pulses correspond to times that the pulse oximeter's 52 individual LEDs 70,74 are activated. Alternatively, photodetectors may be selected to detect only visible light (red LED) and only IR light. The output of these detectors may be transmitted directly to the analog circuit without the need for a logic circuit.

Figure 4:
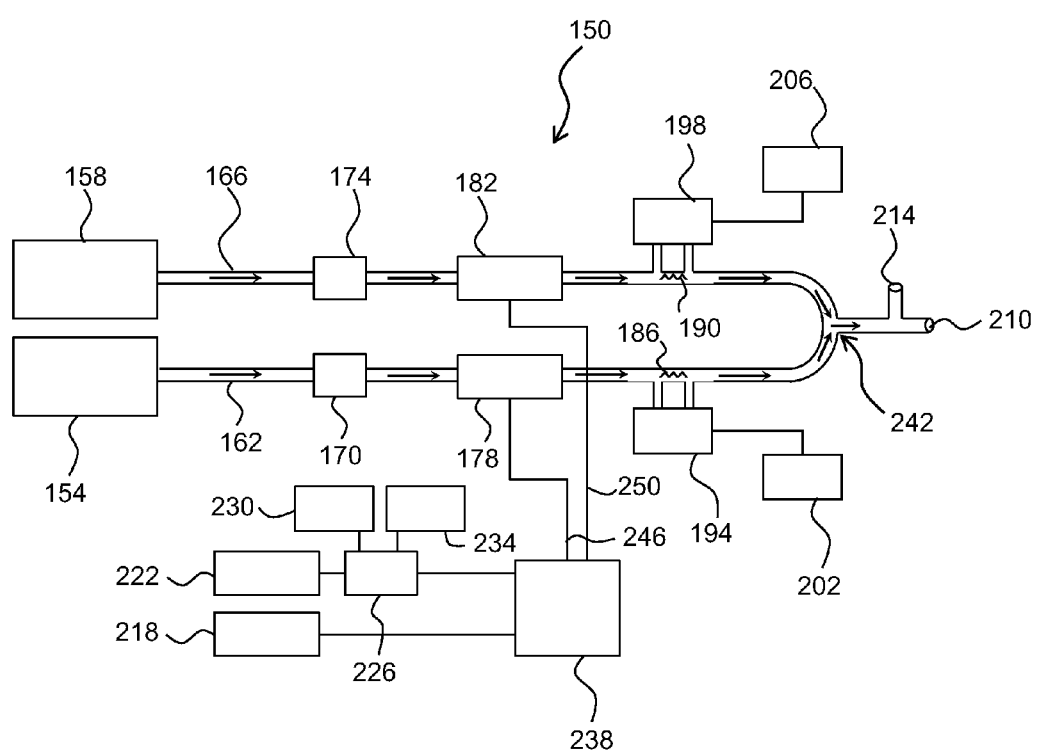
FIG. 4 shows aspects of a $CO_2$ delivery system according to principles of the present invention.

Turning now to FIG. 4, which shows aspects of a $CO_2$ delivery system, generally indicated at 150, according to principles of the present invention. The concentration or partial pressure of carbon dioxide ($CO_2$) may be ascertained by noninvasive respiratory monitors, e.g. a capnometer, and produce a graph of the $CO_2$ concentration in the patient's breath, i.e. a capnogram. The rate of changes in concentration from high to low, or vice versa, may indicate the respiratory rate, adequacy of breathing, and metabolic function. For example, a high concentration of maximum $CO_2$ during the breath may indicate that breathing is inadequate. The shape of the capnogram may be indicative of various breathing abnormalities such as uneven lung emptying, obstructed airways, etc. Thus, to simulate these disease states a training simulator needs to be able to provide a signal that may be varied in order to produce different capnograms.

The $CO_2$ delivery system 150 may include an air source simulation system which creates a $CO_2$ concentration waveform by injecting $CO_2$ gas into a known flow of air. The system may periodically update the amount of $CO_2$ injected. For example the amount of $CO_2$ injected may be updated multiple times each second to re-create the exact shape of a desired waveform.

The baseline air flow into which the $CO_2$ is injected may be provided from an outside source 154 (tank or compressor) and regulated to about 25 PSI along a flow path 162. The air flow can be turned off and on under computer control using, for example, a control valve 178 such as a solenoid valve (e.g. a Clippard EV-2-12, manufactured by Clippard Instrument Lab Inc., Cincinnati, Ohio). The $CO_2$ source 158 may be a tank or cartridge containing compressed 100% carbon dioxide gas. The $CO_2$ gas may be regulated to about 25 PSI along a flow path 166 and passed through a control valve such as a variable orifice valve (e.g. a Clippard EV-10-0925 manufactured by Clippard Instrument Lab Inc., Cincinnati, Ohio). The control valves 178, 182 may be under computer control. The amount of valve opening may be proportional to the electrical current that is delivered to the control valves 178, 182. For example, the computer system 40 may include a digital to analog controller 226 for controlling valve 182. The amount of opening of the variable valve 182 may control the amount of added $CO_2$ and therefore the concentration of $CO_2$ observed by the $CO_2$ gas analyzer connected downstream. The two gas streams may be mixed together at 242 to create a flowing gas mixture from which a clinical $CO_2$ monitoring device (not shown) can draw a continuous sample from port 214.

It has been observed that for a given control voltage (current) the amount of $CO_2$ that exits the variable valve 182 may be different depending on whether the concentration of $CO_2$ is rising or falling. It has also been observed that, because of nonlinearity, the response of the variable orifice valve 182 to a change in voltage may be different depending on the flow rate. To correct for observed hysteresis and/or non-linearity of the $CO_2$ control valve 182 and/or air control valve 178, the system 150 may include flow sensors 194, 198.

According to one aspect of the invention, flow sensors 194, 198 may be incorporated downstream from the $CO_2$ control valve 182 and/or air control valve 178. The flow sensors 194, 198 may comprise flow restrictors 186, 190 through which the gas flows. The flow sensors 194, 198 may measure the pressure difference created by the flowing gas on either side of the flow restrictors 186, 190. The output of the flow sensors 194, 198 may be sent to a computer system 40. More particularly output of the flow sensors 194, 198 may be sent to microprocessors 202, 206 which are part of the computer system 40. The computer system 40 may then use the information to make adjustments to the signals 250, 246 sent to the $CO_2$ control valve 182 and/or air control valve 178 respectively. Thus, the computer system may adjust the ratio of $CO_2$ flow to oxygen flow such that a desired concentration of $CO_2$ is delivered to the $CO_2$ monitoring device.

The computer system 40, which may be used to control the concentration of $CO_2$ which is delivered to the $CO_2$ monitoring device, may include several components in addition to the microprocessors 202, 206 described above. For example, the computer system 40 may include one or more serial peripheral interface buses ("SPI"), such as a SPI clock 234 configured to be output, a SPI master output, slave input ("MOSI") 230 configured to be output, and/or a SPI select device 222 configured to be output. The SPI components may be in communication with a digital to analog controller 226, which may be used to control a variable orifice valve 182. Furthermore, the computer system 40 may include a digital controller 218, which may be used to control a solenoid valve 178. The computer system 40 may also include a valve driver circuit 238 to communicate with both the variable orifice valve 182 and the solenoid valve 178.

Figure 5:
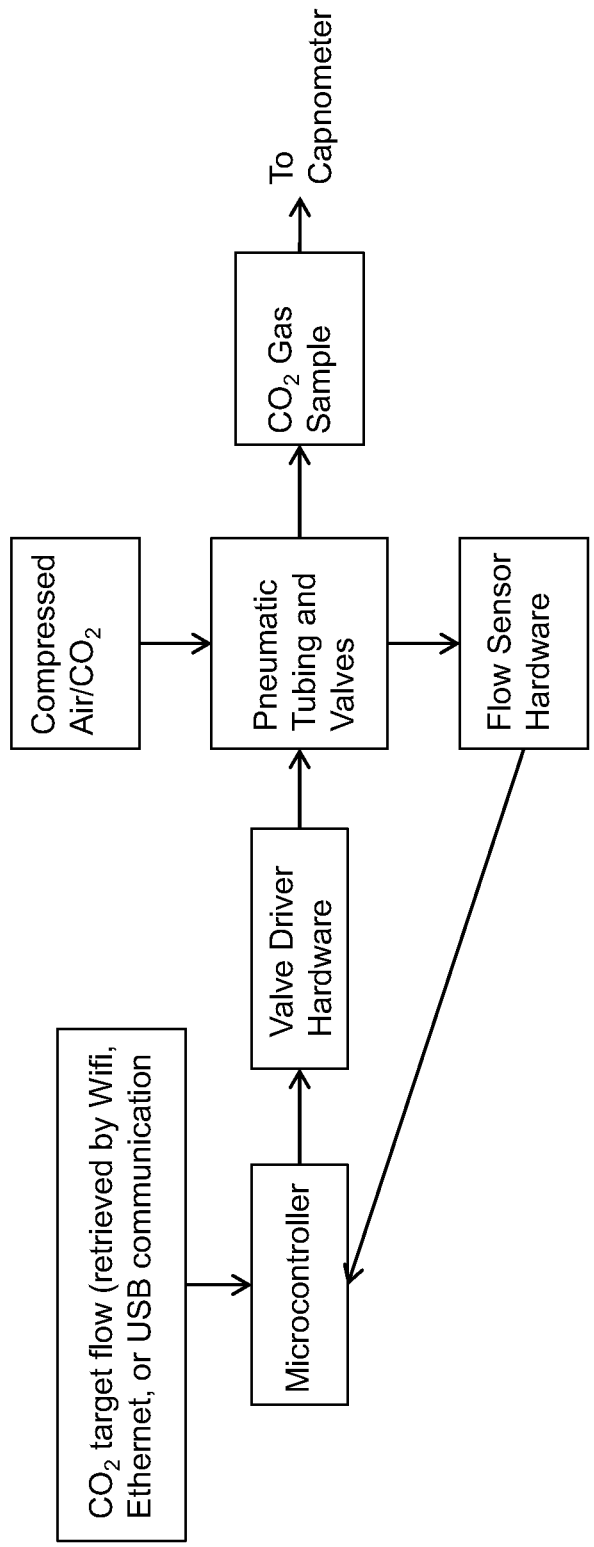
FIG. 5 shows a schematic of how a $CO_2$ delivery system may control the concentration of $CO_2$ which is delivered to a non-invasive respiratory monitor according to one aspect of the present invention.

FIG. 5 shows a schematic of how a $CO_2$ delivery system may control the concentration of $CO_2$ which is delivered to a non-invasive respiratory monitor according to one aspect of the present invention. A $CO_2$ valve control algorithm may be used by the computer system to make adjustments to the ratio of $CO_2$ flow to oxygen flow. For example, a $CO_2$ valve control algorithm may set the $CO_2$ variable orifice valve 182 set to zero flow upon startup, and turn off the air valve 178. After an initialization phase, a microcontroller may rapidly repeat (e.g. about every 40 milliseconds) the following steps:
1) Update Input Queue with new target $CO_2$ flow Values: $CO_{2flow,tgt}$=Dequeue set CO2 value at front of Queue
2) Measure $co2_{delta\_pressure}$=A/D reading of differential Flow sensor (0-5 VDC)
3) Measure $air_{delta\_pressure}$=A/D reading of air Flow sensor (0-5 VDC)
4) Determine $CO_{2flow,meas}$=$CO2_{delta\_pressure}$/($co2_{delta\_pressure}$+$air_{delta\_pressure}$)
5) Update set voltage for $CO_2$ valve:
   a) $\Delta_{flow,absolute}$=abs($CO_{2flow,tgt}$-$CO_{2flow,meas}$)
      i) If ($\Delta_{flow,absolute}$<0.005), change in set voltage for $CO_2$ valve=0
      ii) If ($\Delta_{flow,absolute}$>0.05), change in set voltage $CO_2$ valve=0.61%
      iii) If (0.05>$\Delta_{flow,absolute}$>0.03), change in set voltage for $CO_2$ valve=0.29%
      iv) If (0.03>$\Delta_{flow,absolute}$>0.02), change in set voltage for $CO_2$ valve=0.24%
      v) If (0.02>$\Delta_{flow,absolute}$>0.01), change in set voltage for $CO_2$ valve=0.12%
      vi) If (0.01>$\Delta_{flow,absolute}$>0.005), change in set voltage for $CO_2$ valve=0.06%
   b) If $CO_{2flow,tgt}$>$CO_{2flow,meas}$: increase set voltage for $CO_2$ valve by amount determined in 5a
   c) If $CO_{2flow,tgt}$<$CO_{2flow,meas}$: decrease set voltage for $CO_2$ valve by amount determined in 5a
6) If $CO_2$ valve voltage>0, Air valve is set on, otherwise air valve is set off It will be appreciated that the specific algorithm described above is provided for exemplary purposes only and in no way limits the scope of the present invention.

A targeted $CO_2$ concentration may be achieved through a calibration procedure that relates the set $CO_2$ flow to the measured $CO_2$ concentration. Flow may be set over several values and the measured $CO_2$ recorded. Linear polynomial regression may then be performed to find the best fit.

There is thus disclosed an improved system for generating noninvasive respiratory monitor signals. It will be appreciated that numerous changes may be made to the present invention without departing from the scope of the claims.

What is claimed is:

1. A system for generating simulated noninvasive respiratory monitor signals comprising:
   a pulse oximetry simulation device configured to generate a first signal that is detectable by a noninvasive respiratory monitor;
   a $CO_2$ delivery system configured to generate a second signal that is detectable by a noninvasive respiratory monitor, wherein the second signal that is detectable by a noninvasive respiratory monitor is a flow of air having a concentration of $CO_2$;
   a control valve configured to deliver the concentration of $CO_2$ in the flow of air and wherein the control valve is configured to deliver a variable flow of $CO_2$;
   a computer system disposed in communication with the pulse oximetry simulation device and the $CO_2$ delivery system, wherein the computer system is configured to digitally control the potentiometer to thereby modulate the first signal and the second signal;
   wherein the pulse oximetry simulation device further comprises one or more photodetectors and a LED, and wherein the first signal that is detectable by the noninvasive respiratory monitor is light emitted from the LED; and
   wherein the digitally controlled potentiometer is in electrical communication with the LED, and wherein the digitally controlled potentiometer is configured to modulate the intensity of the light emitted by the LED.

2. The system for generating noninvasive respiratory monitor signals according to claim 1, further comprising a flow sensor, wherein the flow sensor is in communication with the control valve to control the concentration of $CO_2$ in the flow of air.

3. A system for generating simulated noninvasive respiratory monitor signals comprising:
   a pulse oximetry simulation device configured to generate a first signal that is detectable by a noninvasive respiratory monitor;
   a $CO_2$ delivery system configured to generate a second signal that is detectable by a noninvasive respiratory monitor, wherein the second signal that is detectable by a noninvasive respiratory monitor is a flow of air having a concentration of $CO_2$;
   a control valve;
   a first flow sensor for measuring the pressure of air along a first flow path and a second flow sensor for measuring the pressure of $CO_2$ along a second flow path; and
   a computer system disposed in communication with the pulse oximetry simulation device and the $CO_2$ delivery system, wherein the computer system is configured to digitally control the potentiometer to thereby modulate the first signal and the second signal;

wherein the pulse oximetry simulation device further comprises one or more photodetectors and a LED, and wherein the first signal that is detectable by the noninvasive respiratory monitor is light emitted from the LED;

wherein the digitally controlled potentiometer is in electrical communication with the LED, and wherein the digitally controlled potentiometer is configured to modulate the intensity of the light emitted by the LED.

4. The system for generating noninvasive respiratory monitor signals according to claim 3, further comprising a control valve, wherein the computer system produces a signal that is sent to the control valve, the signal being adjustable and dependent on the ratio of the measured pressure of air and the measure pressure of $CO_2$.

* * * * *